United States Patent [19]

O'Young et al.

[11] Patent Number: 5,523,509

[45] Date of Patent: Jun. 4, 1996

[54] MANGANESE OXIDE OCTAHEDRAL MOLECULAR SIEVE AS ACID-BASE CATALYST

[75] Inventors: Chi-Lin O'Young, Poughkeepsie; Robert A. Sawicki, Stormville, both of N.Y.; Yan-Fei Shen; Steven L. Suib, both of Storrs, Conn.

[73] Assignee: Texaco Inc., White Plains, N.Y.

[21] Appl. No.: 335,319

[22] Filed: Nov. 7, 1994

[51] Int. Cl.$^6$ ............................. C07C 1/00; C07C 49/00
[52] U.S. Cl. .......................... 585/640; 585/639; 568/303
[58] Field of Search ................................... 585/640, 639; 568/303

[56] References Cited

U.S. PATENT DOCUMENTS

| | | |
|---|---|---|
| 3,214,236 | 10/1965 | Weisz . |
| 3,779,898 | 12/1973 | Youngblood . |
| 4,373,109 | 2/1983 | Olah . |
| 4,472,593 | 9/1984 | Slaugh et al. . |
| 5,340,562 | 8/1994 | O'Young et al. ........................ 423/599 |

OTHER PUBLICATIONS

Giovanoli et al., "A New Synthesis of Hollandite, A Possibility for Immobilization of Nuclear Waste", *Chimia*, 35, (1981) pp. 53–55 no month available.

Shen et al., "Manganese Oxide Octahedral Molecular Sieves: Preparation, Characterization, and Applications", *Science*, Apr. 23, 1993, vol. 260, pp. 511–515.

Yin et al., "Temperature Program Desorption and Reduction Studies of Octahedral Molecular Sieves", J. Weitkamp et al. (Eds.) *Zeolites and Related Microporous Materials: State of the Art 1994* Studies in Surface Science and Catalysis, vol. 84, 1994 Elsevier Science B.V. no month available.

Chi–Lin O'Young, "Hydrothermal Synthesis of Manganese Oxides with Tunnel Structures", *Synthesis of Microporous Materials*, vol. II, pp. 333–340, M. L. Occelli, H. S. Robson Eds., Van Nostrand Reinhold, NY, 1992 no month available.

De Guzman et al., "Role of Cyclic Voltammetry in Characterizing Solids: Natural and Synthetic Manganese Oxide Octahedral Molecular Sieves", *Chemistry of Materials*, American Chemical Society, 1993, vol. 5, pp. 1395–1400 no month available.

Shen et al., "Octahedral Molecular Sieves: Preparation, Characterization and Applications", *J. Chem Soc., Chem Communications*, Issue 17, 1991, pp. 1213–1214 no month available.

Shen et al., "Synthetic Todorokite: Preparation, Characterization and Applications", *Ninth International Zeolite Conference, Extended Abstracts and Program*, Higgins et al. Eds., 1992, RP230 no month available.

Shen et al., "Synthesis of Manganese Oxide Octahedral Molecular Sieves (OMS)", *Zeolites and Microporous Crystals*, 1994, pp. 19–24 no month available.

Turner et al., "Todorokites: A New Family of Naturally Occurring Manganese Oxides", *Science*, vol. 212, pp. 1024–1027, 29 May 1981.

*Primary Examiner*—E. Rollins Cross
*Assistant Examiner*—E. D. Irzinski
*Attorney, Agent, or Firm*—George J. Darsa; Kenneth R. Priem; Dominick G. Vicari

[57] ABSTRACT

Synthetic manganese oxide octahedral molecular sieves, e.g., OMS-1 and OMS-2, are employed as acid-base catalysts in a variety of acid-base organic conversion reactions.

22 Claims, 3 Drawing Sheets

5,523,509

MANGANESE OXIDE OCTAHEDRAL MOLECULAR SIEVE AS ACID-BASE CATALYST

BACKGROUND OF THE INVENTION

This invention relates to the use of a synthetic manganese oxide octahedral molecular sieve as acid-base catalyst in a wide variety of catalyzed organic conversion reactions.

Manganese oxide octahedral molecular sieves (OMS) possessing mono-directional tunnel structures constitute a family of molecular sieves wherein chains of $MnO_6$ octahedra share edges to form tunnel structures of varying sizes. Such materials have been detected in samples of terrestrial origin and are also found in manganese nodules recovered from the ocean floor. Manganese nodules have been described as useful catalysts in the oxidation of carbon monoxide, methane and butane (U.S. Pat. No. 3,214,236), the reduction of nitric oxide with ammonia (*Atmospheric Environment*, Vol. 6, p.309 (1972)) and the demetallation of topped crude in the presence of hydrogen (*Ind. Eng. Chem. Proc. Dev.1*, Vol. 13, p.315 (1974)).

The hollandites are naturally occurring hydrous manganese oxides with tunnel structures (also described as "framework hydrates") in which Mn can be present as $Mn^{4+}$ and other oxidation states, the tunnels can vary in size and configuration and various mono- or divalent cations can be present in the tunnels. The hollandite structure consists of double chains of $MnO_6$ octahedra which share edges to form (2×2) tunnel structures. The average size of these tunnels is about 4.6 Å square. Ba, K, Na and Pb ions are present in the tunnels and coordinated to the oxygens of the double chains. The identity of the tunnel cations determines the mineral species. Specific hollandite species include hollandite ($BaMn_8O_{16}$), cryptomelane ($KMn_8O_{16}$), manjiroite ($NaMn_8O_{16}$) and coronadite ($PbMn_8O_{16}$).

The hydrothermal method of synthesizing a manganese oxide octahedral molecular sieve possessing (2×2) tunnel structures similar to the naturally-occurring hollandites is described in "Hydrothermal Synthesis of Manganese Oxides with Tunnel Structures," in *Synthesis of Microporous Materials*, Vol, II, 333, M. L. Occelli, H. E. Robson Eds. Van Nostrand Reinhold, N.Y., 1992. Such synthetic octahedral molecular sieves having (2×2) tunnel structures are referred to in the art by the designation OMS-2. The (2×2) tunnel structure of OMS-2 is diagrammatically depicted in FIG. 1A.

The hydrothermal method of producing OMS-2 involves autoclaving an aqueous solution of manganese cation and permanganate anion under acidic conditions, i.e., pH<3, at temperatures ranging from about 80 to about 140° C. in the presence of counter cations having ionic diameters of between about 2.3 and about 4.6 Å. The counter cations serve as templates for the formation of OMS-2 product and can be retained in the tunnel structures thereof. Based on analytical tests, OMS-2 produced via this method is thermally stable up to about 600° C.

Alternatively, OMS-2 can be produced by the method disclosed in R. Giovanili and B. Balmer, *Chimia*, 35 (1981) 53. Thus, when manganese cation and permanganate anion are reacted under basic conditions, i.e., pH>12, a layered manganese oxide precursor is produced. This precursor is ion exchanged to form another layered manganese oxide which is then calcined at high temperatures, i.e., temperatures generally exceeding about 600° C., to form OMS-2 product. Analytical tests indicate that OMS-2 produced via this method is thermally stable up to about 800° C. and the average oxidation state of manganese ion is lower.

The todorokites are naturally occurring manganese oxides with (3×3) tunnel structures formed by triple chains of $MnO_6$ edge-sharing octahedra. Todorokites and related species are described by Turner et al. in "Todorokites: A New Family of Naturally Occurring Manganese Oxides", *Science*, Vol. 212, pp. 1024–1026 (1981). The authors speculate that since todorokites are often found in deep-sea manganese nodules containing high concentrations of copper and nickel, it is probable that such metals substitute for $Mn^{2+}$ in the octahedral framework.

Todorokites have attracted particular interest because of their relatively large tunnel dimension and their cation-exchange behavior which is similar to that of zeolites (Shen et al., "Manganese Oxide Octahedral Molecular Sieves: Preparation, Characterization, and Applications", *Science*, Vol. 260, pp. 511–515 (1993)). The naturally occurring todorokites are poorly crystalline, impure in composition and coexist with other manganese oxide minerals. Results of high resolution transmission electron microscopy (HRTEM) show that todorokite contains random intergrowth material of 3×2, 3×3, 3×4 and 3×5 tunnel structures. Because of their disordered structure, the todorokites exhibit variable and non-reproducible catalytic activity, a drawback which militates against their commercial use.

A method of synthesizing a manganese oxide octahedral molecular sieve possessing (3×3) tunnel structures similar to the naturally-occurring todorkites is described in U.S. Pat. No. 5,340,562. Such synthetic octahedral molecular sieves having (3×3) tunnel structures are referred to in the art by the designation OMS-1. The (3×3) tunnel structure of OMS-1 is diagrammatically depicted in FIG. 1B.

OMS-1 can be prepared by reacting manganese cation and permanganate anion under strongly basic conditions to form a layered manganese oxide precursor, thereafter aging the precursor at room temperature for at least 8 hours, ion exchanging the aged precursor and then autoclaving the ion-exchanged precursor at from about 150 to about 180° C. for several days. Analytical tests indicate that OMS-1 produced via this method is thermally stable up to about 500° C.

Methods of substituting the frameworks of OMS-1 and OMS-2 with a metal other than manganese are described in commonly assigned, copending U.S. Appln. Ser. No. 08/215,496, filed Mar. 21, 1994.

SUMMARY OF THE INVENTION

In accordance with the present invention, an acid-base organic conversion reaction is catalyzed by a synthetic manganese oxide octahedral molecular sieve possessing both acidic and basic sites.

The process of this invention is carried out by contacting at least one organic reactant with synthetic manganese oxide octahedral molecular sieve as catalyst under acid-base conversion reaction conditions to provide at least one organic conversion product. Reaction conditions such as temperature, pressure, and so forth, can be varied depending on the particular organic reactant and OMS catalyst being employed and on the conversion product which is desired.

The catalyst itself can be any synthetic OMS possessing mono-directional tunnel structures such as those found in the naturally-occurring hollandites and todorokites, for example, OMS-2 and OMS-1. Manganese oxide octahedral molecular sieves substituted with metal cation(s) in the tunnel structures and/or frameworks thereof can be employed.

Unlike the naturally-occurring hollandites and todorokites, synthetic manganese oxide octahedral molecular sieve employed as catalyst in the method of this invention possesses a highly uniform and homogeneous structure, i.e., one made up substantially entirely of a single tunnel structure species without admixture of any significant amount of other tunnel structure species. As such, the synthetic manganese oxide octahedral molecular sieve employed in the acid-base conversion process herein provides consistent and reproducible results for a given type of conversion process and conversion conditions, benefits which have heretofore not been attainable employing naturally-occurring manganese oxides with their mixed tunnel structure morphologies.

The phrase "organic conversion reaction" shall be understood herein to refer to a wide variety of acid-base reactions including, but not limited to, one or more of the following: hydrocarbon conversions, isomerization, cracking, polymerization, alkylation, acylation, hydration, dehydration, esterification, hydrolysis, hydrocracking, hydrogenation, dehydrogenation, and the like.

The term "OMS" as utilized herein shall be understood to refer to substituted and unsubstituted synthetic manganese oxide octahedral molecular sieves.

DESCRIPTION OF THE PREFERRED EMBODIMENTS

Figure 1A:
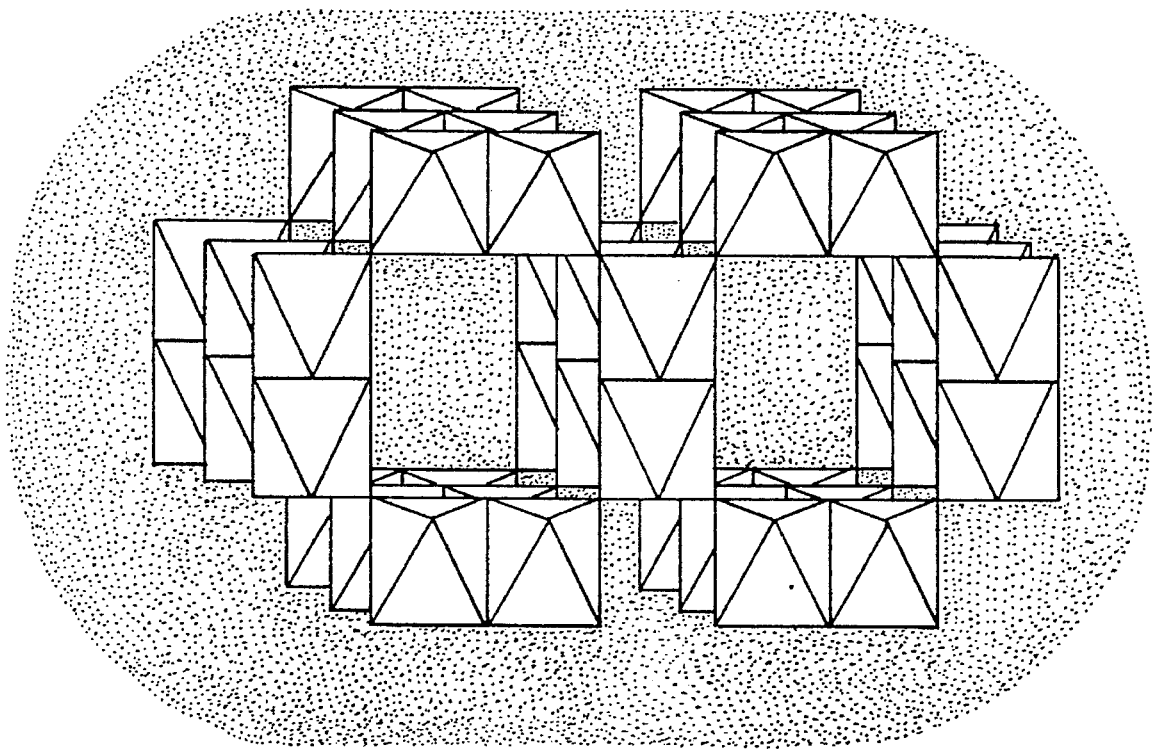
FIGS. 1A and 1B are diagrammatic representations of the three-dimensional tunnel structures of OMS-2 and OMS-1, respectively; and, FIGS. 2a–2e depict x-ray powder diffraction patterns of samples of A-OMS-1 utilized as catalyst in the process of this invention.
Figure 1B:
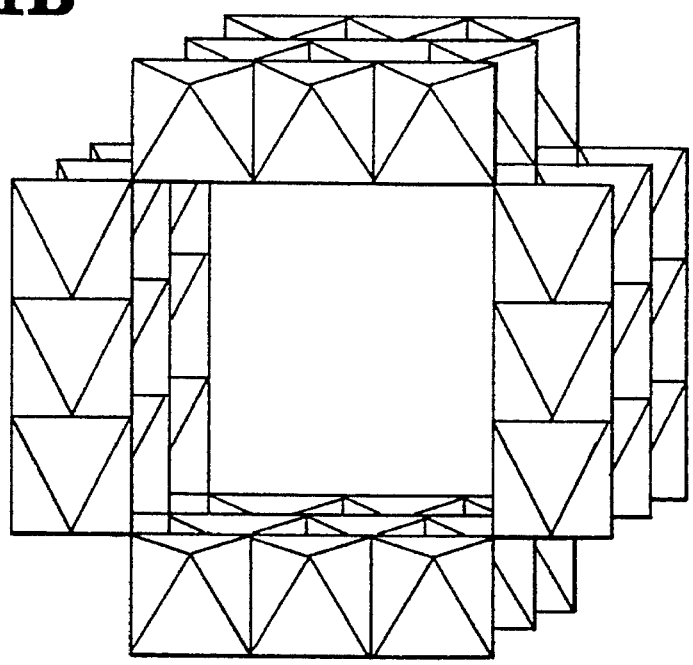

The preferred catalyst utilized herein is a synthetic tunnel-substituted and/or framework-substituted manganese oxide octahedral molecular sieve. Where OMS-2 is employed the catalyst will correspond to the general formula:

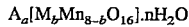
$$A_a[M_bMn_{8-b}O_{16}] \cdot nH_2O$$

wherein A is a +1, +2, +3 or +4 tunnel cation or combination thereof, $0 \leq a \leq 4$, M is a +1, +2, +3 or +4 framework-substituting metal cation or combination thereof, $0 \leq b \leq 8$ and $n \geq 0$. Where OMS-1 is employed the catalyst will correspond to the general formula:

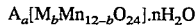
$$A_a[M_bMn_{12-b}O_{24}] \cdot nH_2O$$

wherein A is a +1, +2, +3 or +4 tunnel cation or combination thereof, $0 \leq a \leq 6$, M is a +1, +2, +3 or +4 framework-substituting metal cation or combination thereof, $0 \leq b \leq 12$ and $n \geq 0$.

The framework-substituting metal cation(s), M, can be a transition metal selected from Groups IIIA, IVA, VA, VIA, VIIA, VIIIA, IB and IIB of the Periodic Table of the Elements. Examples of useful framework-substituting metals include Mg, Fe, Co, Ni, Cu, Ti, V, Cd, Mo, W, Cr, Zn, La, Ir, Rn, Pd and Pt. Preferred metals include Co, Cu, Ni, Zn, La and Pd. The tunnel cation(s), A, can be alkali metal cations, alkaline earth metal cations and transition metal cations which facilitate the selection, formation and stabilization of desired OMS products. Thus, the tunnel cations can serve as templates for crystallization of the products. The ionic diameters of some alkali and alkaline earth metal cations which can be employed are listed below:

| Cation | $Li^+$ | $Na^+$ | $K^+$ | $Cs^+$ | $Mg^{2+}$ | $Ca^{2+}$ | $Ba^{2+}$ |
|---|---|---|---|---|---|---|---|
| r(Å) | 1.36 | 1.96 | 2.66 | 3.78 | 1.30 | 1.98 | 2.70 |

Examples of transition metal cations which can be employed include Co, Ni, Cu and Zn.

The method of synthesis of a manganese oxide octahedral molecular sieve utilized herein will depend on whether OMS-1 or OMS-2 is desired. The methods of making OMS-1 and OMS-2 have in common a first step of reacting manganese cation and permanganate anion optionally together with framework-substituting metal cation(s) in an aqueous reaction medium. When the reaction is carried out under acidic conditions and autoclaved at temperatures ranging from about 80° to about 140° C. in the presence of counter cations having ionic diameters of between about 2.3 and about 4.6 Å, OMS-2 is formed. Alternatively, when the reaction is carried out under strongly basic conditions a layered manganese oxide precursor is formed. OMS-2 is formed when this precursor is ion exchanged and calcined at high temperatures. In contrast, OMS-1 is formed when this precursor is aged at room temperature for at least about 8 hours, ion exchanged and thereafter autoclaved at from about 150 to about 180° C. for several days. Examples for producing specific substituted synthetic manganese octahedral molecular sieves which may be employed in the method of this invention are presented hereinbelow.

Due to their regular pore size, synthetic manganese oxide octahedral molecular sieves exhibit shape selectivity similar to the well-known zeolite catalysts. Thus, the catalysts can adsorb most organic molecules. The process of this invention takes advantage of the bifunctional property of synthetic manganese oxide octahedral molecular sieves derived from having both acidic and basic sites in the structure thereof. Therefore, synthetic manganese oxide octahedral molecular seive catalysts herein can be utilized as acidic catalysts, i.e., as Brønsted acids (proton donors) and/or as Lewis acids (electron pair acceptors) and as basic catalysts, i.e., as Brønsted bases (proton acceptors) and/or as Lewis bases (electron pair donors).

In a preferred embodiment of the method of this invention, an alkanol is converted to a ketone and an olefin in the presence of synthetic manganese oxide octahedral molecular sieves as catalyst under acid-base organic conversion reaction conditions. Conversion of the alkanol to a ketone involves dehydrogenation which occurs on basic sites within the synthetic manganese oxide octahedral molecular sieve catalyst. Conversion of the alkanol to an olefin involves dehydration which occurs on acidic sites within the synthetic manganese oxide octahedral molecular sieve catalyst. In a particularly preferred embodiment, the alkanol is isopropanol, the ketone is acetone and the olefin is propylene. In accordance with this embodiment, the manganese oxide octahedral molecular sieve catalyst can be utilized in fluidized beds or packed columns, preferably the latter. The feedstock containing isopropanol can contain minor amounts of water, for example, amounts of up to about twenty-five percent by weight, preferably no more than up to about fifteen percent by weight, present therein. The reactor is operated within the temperature range of from about 200° C. to about 500° C., preferably from about 250°

C. to about 450° C. The alcohol is fed to the reactor at space velocities ranging from about 0.01 to about 10, preferably from about 1.0 to about 5, ml/sec-g. Reactor pressure is maintained at from about atmospheric to about 1000 psi, preferably from about atmospheric to about 250 psi.

Although hydrogen is generated in the reaction, the presence of an external supply of hydrogen is desirable to prevent the OMS catalyst from rapidly losing activity as a function of time. It is desirable to maintain the partial pressure of hydrogen at from about 5 to about 800 psi, and preferably from about 15 to about 250 psi in the reactor. Molar ratios of hydrogen to isopropanol of greater than about 3 are desirable.

The reaction may be conducted batchwise or in a continuous operation. By way of illustration of the batchwise process, a high pressure autoclave containing OMS catalyst is charged with isopropanol and pressurized with hydrogen and heated to reaction temperature. After the reaction is allowed to proceed for the desired length of time, the autoclave is cooled, the excess hydrogen vented, and the acetone and propylene reaction products worked up by conventional methods. By way of illustration of continuous operation, a vertical, high-pressure column is charged with OMS catalyst and isopropanol is supplied at one end of the column. At the same time hydrogen is metered into the column in concurrent flow. During the reaction, appropriate conditions of temperature and pressure are maintained. The acetone and propylene reaction products are removed from the bottom of the column, freed from hydrogen and worked up by conventional methods. The hydrogen is advantageously recycled to the reactor.

Synthetic manganese oxide octahedral molecular sieves utilized herein can be bound within a matrix or binder, e.g., alumina, silica-alumina, clay or admixtures thereof, to provide a support for the OMS component. Normally, the composited catalyst can contain at least about 10 up to about 85 weight percent of such a binder or matrix. The alumina which can be used as the matrix material of the composited catalyst utilized in the method of the present invention can be any suitable grade of crystalline or amorphous alumina which is substantially inert.

The synthetic manganese oxide octahedral molecular sieve can be composited with the matrix or binder in a variety of ways, e.g., by adding the OMS to a silica-alumina slurry, spray drying the mixture, washing the resultant solid product and drying. Optionally, a clay diluent can be present in the silica-alumina slurry. Such matrixes can be prepared by admixing colloidal alumina (boehmite) and colloidal silica and allowing the matrix properties to vary over a wide range from catalytically inert to active. The activity, thermal stability, surface area and pore distribution of the matrix can be controlled by varying the amounts and particle size distributions of the respective colloids. In the section by Magee and Blazek on "Zeolite Cracking Catalysts" in ACS Monograph 171, *Zeolite Chemistry and Catalysts*. (J. Rabo, Ed.; Am. Chem. Soc., Wash, D.C. 1976), guidance for the preparation of catalysts containing high porosity matrices such as silica-alumina can be found.

The synthetic manganese oxide octahedral molecular sieve catalyst can be composited with a porous clay matrix material which has suitable binding properties and is resistant to the temperature and other conditions employed in the acid-base organic conversion reaction. The composite is then calcined to confer the required physical strength. Naturally occurring clays can be composited with the OMS catalyst and these clays can be used in the raw state as originally mined or initially subjected to calcination, acid treatment, chemical modification or purification.

Examples of suitable clays which can be used include the bentonite and kaolin families. Bentonites are mixtures of clays, mainly montmorillonites, which may also contain kaolinite clays. The Wyoming bentonites and montmorillonites are preferred because of their relatively high purity. Kaolin clays include, for example, the Dixie, McNamee-Georgia and Florida clays and others in which the main mineral constituent is halloysite, kaolinite, dickite, nacrite or anuxite. Other clays may also be found to be suitable for use in the present process.

The amount of clay or other matrix material relative to OMS in the composite will determine, to a certain extent, the physical strength of the final catalyst, especially its attrition resistance and crushing strength. The mechanical properties of the catalyst can therefore be modified by appropriate choice of matrix/OMS ratio, with greater amounts of matrix generally conferring better mechanical properties. On the other hand, larger amounts of matrix mean that less of the OMS catalyst with its desired attendant properties will be available to participate in the eventual acid-base organic conversion reaction. A balance will therefore be struck, in most cases, between activity and mechanical properties. Normally, the amount of matrix material will not exceed 50 percent by weight of the composite and in most cases it will not exceed 40 percent by weight and may be lower, e.g., 25 percent by weight or even 15 percent by weight.

The manganese oxide octahedral molecular sieve catalyst may conveniently be composited with the clay or other matrix materials by forming an aqueous slurry of OMS with the matrix material, spray drying the slurry to form microspheres and then calcining. Alternatively, extrudates, pellets and beads can be formed from matrix and OMS mixtures.

During the course of the acid-base organic conversion reaction, coke and/or other carbonaceous deposits can accumulate upon the surface and within the pores of the manganese oxide octahedral molecular sieve catalyst. As such accumulations increase, the activity of the catalyst decreases. After a time of continuous operation, the accumulation of carbonaceous deposits will become so great and the catalytic activity of the catalyst will be so low that it is uneconomical to continue operation of the process herein. The catalytic activity of an OMS catalyst containing substantial carbonaceous deposits may be substantially restored by regenerating the catalyst and removing such accumulated carbonaceous deposits from the catalyst. Commonly, the carbonaceous deposits are removed and catalyst activity is regenerated by burning, under controlled conditions, in the presence of an oxygen containing gas. Such regeneration procedures are well known to those familiar with the regeneration of catalyst and need not be further described herein.

It may be convenient to employ a plurality of reaction zones containing manganese oxide octahedral molecular sieves catalysts, such that reaction zones are continuously available for use in the process while other reaction zones are undergoing regeneration to remove carbonaceous deposits therefrom. Upon regeneration of the catalyst in a reaction zone, such zone may be returned to service in the process herein and another zone may be removed from service for regeneration.

The following examples are presented to illustrate specific embodiments of the practice of this invention and are not to be interpreted as limitations upon the scope of this invention.

Examples 1–5: Preparation of Tunnel-Substituted A-OMS-1

Five samples of A-OMS-1, wherein A is a tunnel metal cation of Mg, Co, Ni, Cu or Zn, were prepared as follows:

About 50 mL of 5.0M NaOH solution was added dropwise into 40 mL of 0.50M $MnCl_2$ solution at room temperature under vigorous stirring to prepare a $Mn(OH)_2$ suspension. To the suspension, about 40 mL of 0.1M $Mg(MnO_4)_2$ solution was then added dropwise at room temperature under vigorous stirring. A black brown suspension was obtained. The final pH of the reaction medium was 13.8. After aging the suspension at room temperature for 4 days, the suspension was filtered and washed with water until no $Cl^-$ was detected or until the pH was about 7. In this way, a suspension of a layered $Na^+$-birnessite material was obtained.

Figure 2A:
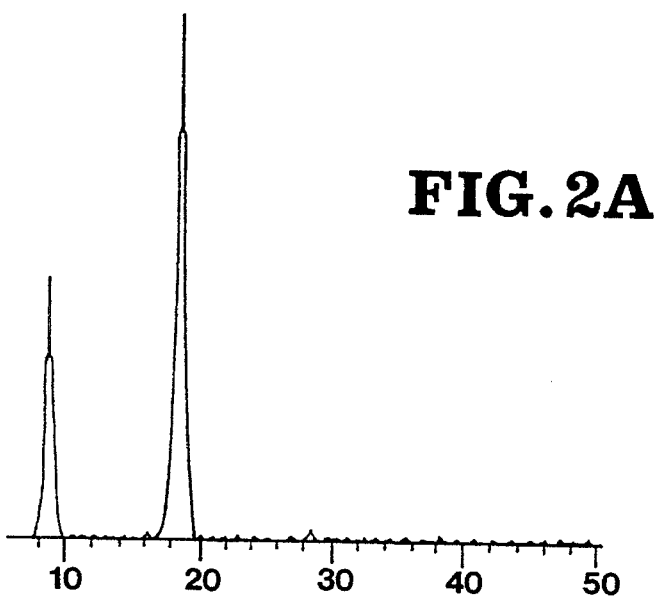
Figure 2B:
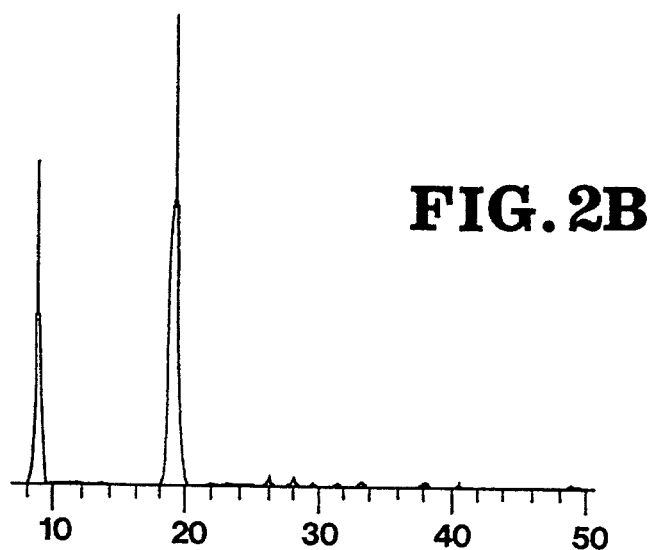
Figure 2C:
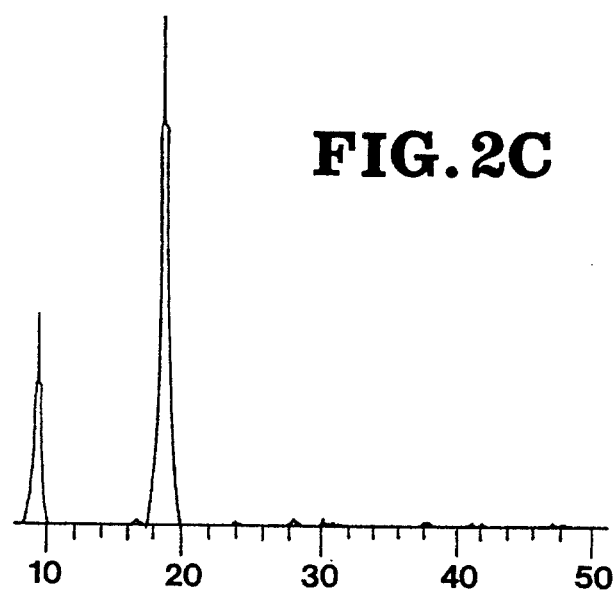
Figure 2D:
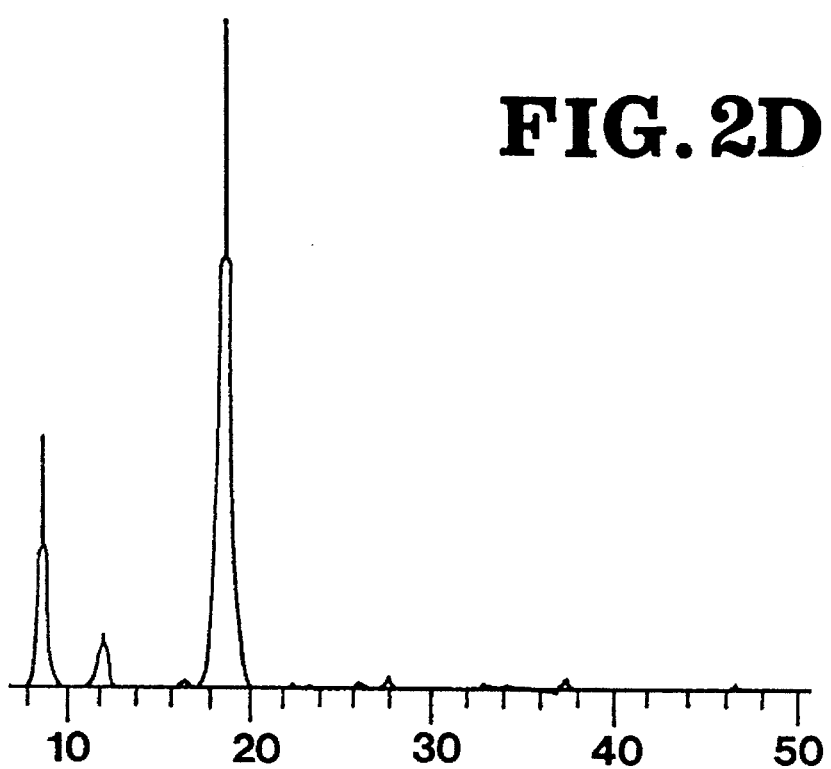
Figure 2E:
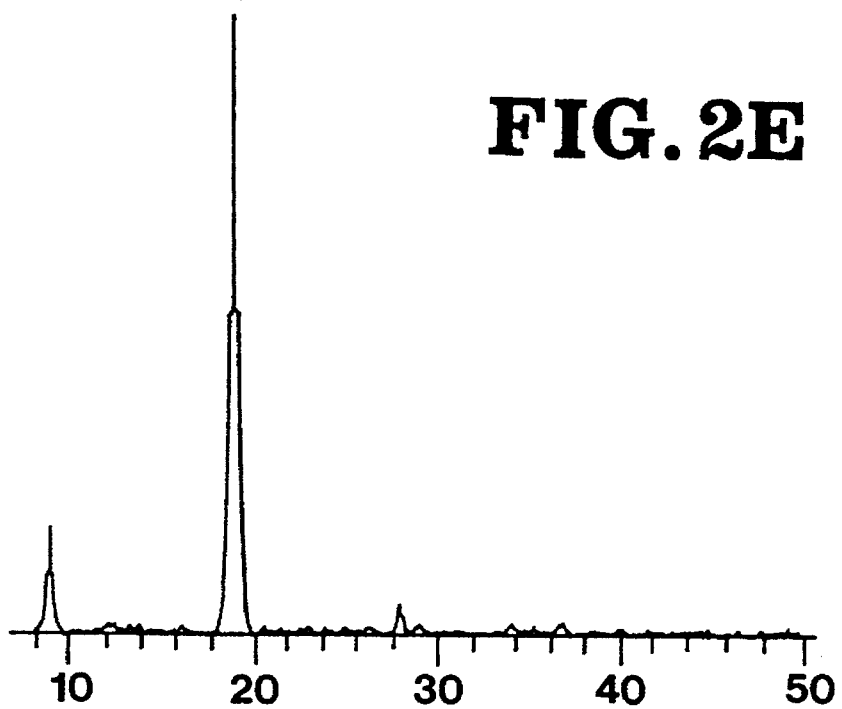

The $Na^+$-birnessite suspension was then separately ion-exchanged with 300 mL of a 0.5–1M aqueous solution of five chloride salts of $Mg^{2+}$, $Co^{2+}$, $Ni^{2+}$, $Cu^{2+}$ and $Zn^{2+}$ at room temperature while stirring overnight. The exchanged product was then filtered and washed with water to provide a suspension of another layered material, i.e., buserite. The buserite suspension was autoclaved at 150°–170° C. for about 2 days to provide five samples of tunnel-substituted A-OMS-1. The product was filtered and washed with water three to five times and dried at room temperature in air. FIGS. 2a–2e show x-ray powder diffraction (XRD) patterns of the resulting five samples of A-OMS-1. All five samples show two diagnostic lines for todorokite at 9.5–9.6 Å and 4.8 Å, respectively. Table 1 shows the composition and average oxidation state of manganese determined by thiosulfate titration.

TABLE 1

Elemental Composition of A—OMS-1 Samples and Average Oxidation State of Mn

| Example | 1 | 2 | 3 | 4 | 5 |
|---|---|---|---|---|---|
| Sample | Mg—OMS-1 | Co—OMS-1 | Ni—OMS-1 | Cu—OMS-1 | Zn—OMS-1 |
| Mn, wt % | 42.5 | 39.4 | 41.9 | 30.6 | 31.5 |
| M, wt % | 11.8 | 13.9 | 12.8 | 27.8 | 29.8 |
| average oxidation state of Mn | 3.50 | 3.64 | 3.60 | 3.82 | 3.78 |

Examples 6–10: Decomposition of Isopropanol on A-OMS-1

The A-OMS-1 samples from Examples 1-5 were individually evaluated for their performance as acid-base catalysts. In separate runs, about 22 mg of each of the aforementioned samples were loaded into a tubular reactor and subjected to isopropanol vapor at a reaction temperature of 260° C. and a space velocity of 4.5 ml/sec-g. Isopropanol vapor was carried through the catalyst at a rate of about 6 mL/min by flowing helium at room temperature. The effluent was analyzed on-line with an HP 5880A series gas chromatograph equipped with a Carbowax column. Table 2 below presents the catalytic data resulting from these tests.

TABLE 2

Isopropanol Decomposition on A—OMS-1 Catalysts

| | | Conversion | Turnover frequency (× 10 − 2 ml/sec-g) | |
|---|---|---|---|---|
| Example | Catalyst | % | Acetone | Propylene |
| 6 | Mg—OMS-1 | 7.0 | 22.9 | 8.6 |
| 7 | Co—OMS-1 | 7.7 | 31.4 | 3.3 |
| 8 | Ni—OMS-1 | 14.1 | 63.0 | 2.4 |
| 9 | Cu—OMS-1 | 93.8 | 422.1 | 0 |

TABLE 2-continued

Isopropanol Decomposition on A—OMS-1 Catalysts

| | | Conversion | Turnover frequency (× 10 − 2 ml/sec-g) | |
|---|---|---|---|---|
| Example | Catalyst | % | Acetone | Propylene |
| 10 | Zn—OMS-1 | 2.8 | 9.4 | 3.2 |

As shown in Table 2, conversion and selectivity to acetone decreases in the following sequence: Cu-OMS-1>>Ni-OMS-1>Co-OMS-1>Mg-OMS-1>Zn-OMS-1, while selectivity to propylene decreases in the sequence Mg-OMS-1, Co-OMS-1>Zn-OMS-1>Ni-OMS-1>>Cu-OMS-1. The conversion of isopropanol to propylene and acetone involves dehydration and dehydrogenation. Dehydration occurs on acid sites within the OMS catalyst and dehydrogenation occurs on basic sites within the OMS catalyst.

What is claimed is:

1. A method for converting at least one alkanol to at least one organic conversion reaction product selected from the group consisting of ketone and olefin which comprises contacting the alkanol with synthetic manganese oxide octahedral molecular sieve as catalyst under acid-base conversion reaction conditions to provide the organic conversion product.

2. The method of claim 1 wherein the alkanol is isopropanol, the ketone is acetone and the olefin is propylene.

3. The method of claim 2 wherein the octahedral molecular sieve is OMS-1.

4. The method of claim 3 wherein OMS-1 is tunnel-substituted with a metal cation selected from the group consisting of Li, Na, K, Cs, Mg, Ca, Ba, Co, Ni, Cu and Zn.

5. The method of claim 1 wherein the reaction conditions include a temperature ranging from about 200° C. to about 500° C.

6. The method of claim 1 wherein the reaction conditions include a temperature ranging from about 350° C. to about 450° C.

7. The method of claim 1 wherein the reaction conditions include a space velocity of about 0.01 to about 10 ml/sec-g.

8. The method of claim 1 wherein the reaction conditions include a space velocity of about 1.0 to about 5 ml/sec-g.

9. The method of claim 1 wherein the reaction conditions include pressure ranging from about atmospheric to about 1000 psi.

10. The method of claim 1 wherein the octahedral molecular sieve is OMS-1 and/or OMS-2.

11. The method of claim 1 wherein the octahedral molecular sieve is combined with a support.

12. The method of claim 11 wherein the support is alumina or silica.

13. The method of claim 1 wherein the octahedral molecular sieve corresponds to the general formula:

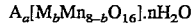

$$A_a[M_bMn_{8-b}O_{16}] \cdot nH_2O$$

wherein A is a +1, +2, +3 or +4 tunnel cation or combination thereof, $0 \leq a \leq 4$, M is a +1, +2, +3 or +4 framework-substituting metal cation or combination thereof, $0 \leq b \leq 8$ and $n \geq 0$.

14. The method of claim 13 wherein the tunnel cation is selected from the group consisting of alkali metal cations, alkaline earth metals and transition metal cations.

15. The method of claim 13 wherein the tunnel cation is selected from the group consisting of Li, Na, K, Cs, Mg, Ca, Ba, Co, Ni, Cu and Zn.

16. The method of claim 13 wherein the framework-substituting metal cation is a transition metal.

17. The method of claim 13 wherein the framework-substituting metal cation is selected from the group consisting of Mg, Fe, Co, Ni, Cu, Ti, V, Cd, Mo, W, Cr, Zn, La, Ir, Rh, Pd and Pt.

18. The method of claim 1 wherein the octahedral molecular sieve corresponds to the general formula:

$$A_a[M_b Mn_{12-b} O_{24}] \cdot nH_2O$$

wherein A is a +1, +2, +3 or +4 tunnel cation or combination thereof, $0 \leq a \leq 6$, M is a +1, +2, +3 or +4 framework-substituting metal cation or combination thereof, $0 \leq b \leq 12$ and $n \geq 0$.

19. The method of claim 18 wherein the tunnel cation is selected from the group consisting of alkali metal cations, alkaline earth metal cations and transition metal cations.

20. The method of claim 18 wherein the tunnel cation is selected from the group consisting of Li, Na, K, Cs, Mg, Ca, Ba, Co, Ni, Cu and Zn.

21. The method of claim 18 wherein the framework-substituting metal cation is a transition metal.

22. The method of claim 18 wherein the framework-substituting metal cation is selected from the group consisting of Mg, Fe, Co, Ni, Cu, Ti, V, Cd, Mo, W, Cr, Zn, La, Ir, Rh, Pd and Pt.

* * * * *